United States Patent [19]
Hakim et al.

[11] 4,332,255
[45] Jun. 1, 1982

[54] SHUNT VALVE

[75] Inventors: Salomon Hakim, Bogota, Colombia; Carlos A. Hakim, Fort Lauderdale, Fla.

[73] Assignee: Hakim Company Limited, Saint Vincent, British West Indies

[21] Appl. No.: 190,018

[22] Filed: Sep. 23, 1980

Related U.S. Application Data

[63] Continuation-in-part of Ser. No. 2,354, Jan. 10, 1979, abandoned.

[51] Int. Cl.³ .............................................. A61M 27/00
[52] U.S. Cl. ................................................. 128/350 V
[58] Field of Search ..................... 128/350 V; 137/539

[56] References Cited
U.S. PATENT DOCUMENTS

| | | | |
|---|---|---|---|
| 1,922,379 | 8/1933 | Longfellow | 137/539 |
| 3,288,142 | 11/1966 | Hakim | 128/350 V |
| 3,527,226 | 9/1970 | Hakim | 128/350 V |
| 3,886,948 | 6/1975 | Hakim | 128/350 V |
| 4,106,510 | 8/1978 | Hakim et al. | 128/350 V |

Primary Examiner—C. Fred Rosenbaum
Attorney, Agent, or Firm—Kenway & Jenney

[57] ABSTRACT

In a surgically implantable shunt system for venting cerebrospinal fluid in the treatment of hydrocephaly, a valve and the method of testing it are disclosed. The valve comprises an elongate hollow valve body into which a flat plate tightly fits, partitioning the valve body into an outlet and an inlet chamber. The flat plate has a circular aperture connecting the chambers and upon which rests a spherical ball of diameter larger than the aperture. A flat spring biases the ball against the circular periphery of the aperture creating a circular seal and providing a precisely defined back pressure, low hysteresis and low susceptiblity to bridging by debris. Testing for leakage is accomplished by illuminating with light of a suitable frequency the aperture with ball seated and detecting any light transmitted therethrough.

7 Claims, 8 Drawing Figures

U.S. Patent  Jun. 1, 1982  Sheet 1 of 2  4,332,255
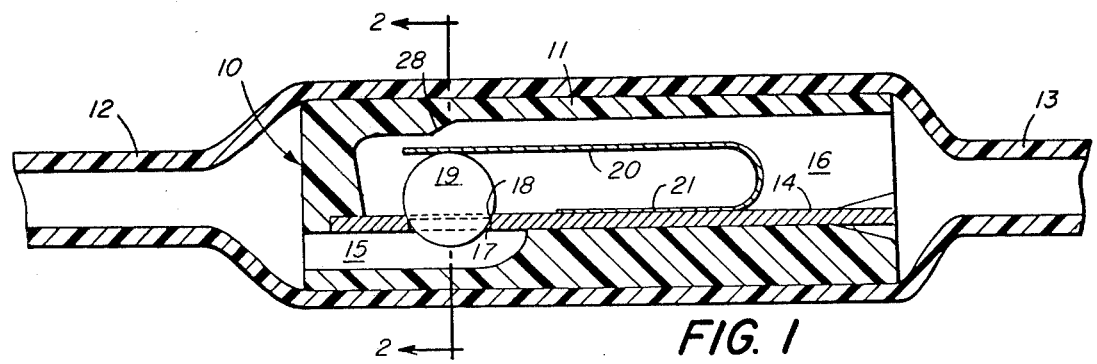
FIG. 1
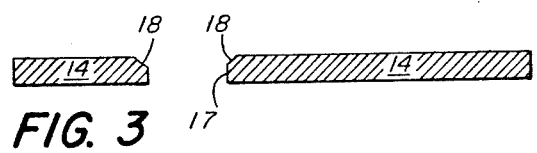
FIG. 3
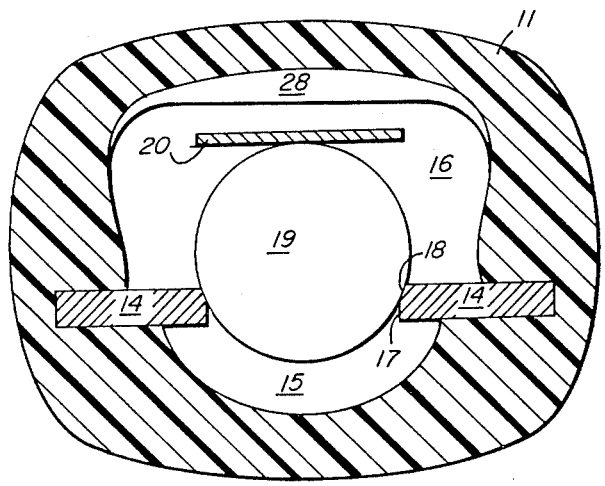
FIG. 2
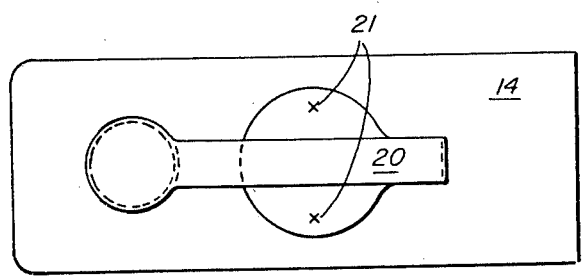
FIG. 4
FIG. 5 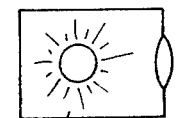  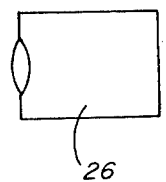

SHUNT VALVE

BACKGROUND OF THE INVENTION

This is a continuation-in-part of U.S. Ser. No. 2,354, filed Jan. 10, 1979, and now abandoned entitled "Shunt Valve".

This invention relates to a valve in a surgically implantable shunt system for venting cerebrospinal fluid (CSF) from a cerebroventricular catheter to a drainage catheter and more particularly to such a valve for presenting a precisely controllable and adjustable back pressure to the cerebral ventricles in case of hydrocephaly and similar conditions of impaired circulation and absorption of cerebrospinal fluid.

Mechanical devices for controlling the drainage of cerebrospinal fluid into the bloodstream are in use, an example of which is the shunt device of U.S. Pat. No. 3,288,142. These devices include valves such that the flow is unidirectional from the ventricles to drainage into the circulatory system. While quite successful, such valves are relatively expensive and difficult to fabricate. These prior valves are also somewhat heavy and bulky, their metal parts interferring, for example, with X-ray scanning procedures. Previously known devices also sometimes become clogged with brain debris or with CSF protein when elevated to abnormally high levels. This is particularly true of so-called slit valves which have been used for this purpose, e.g., valves which are merely a thin slit in a silastic tube. Such debris can prevent the valve from sealing properly, thereby degrading its ability to regulate closely the back pressure presented to the cerebral ventricles. Wide hysteresis between opening and closing pressures has been another shortcoming of known shunt valves for use in treating hydrocephaly, i.e., there has not been a well defined "popping" pressure at which pressure the valve opens. Establishing the desired pressure in known valves has been another area of difficulty.

Testing of known valves has been accomplished previously by subjecting the valves to a vacuum or a gas pressure, or even exposure to a liquid environment. These methods are cumbersome, time consuming and often foul the valve in the testing process.

An object of this invention, therefore, is to develop a simple, highly reliable cerebroventricular shunt valve which is compact, light in weight, minimally opaque to X-rays, and inexpensive to manufacture.

Another object is to produce a shunt valve having low hysteresis and low susceptibility to clogging with debris, enabling it to present a precisely controllable back pressure to the cerebral ventricles.

Yet another object is a shunt valve which allows its operating pressure to be set very accurately.

Still another object is a shunt valve whose operating pressure may be continuously adjusted.

A still further object is to develop a method of testing the sealing effectiveness of such a valve during manufacture by simple optical means.

Other objects, features and advantages of the present invention will become apparent in what follows.

SUMMARY OF THE INVENTION

According to the present invention, a valve for precisely controlling the back pressure presented to the cerebral ventricles in a hydrocephalus shunt device has an elongate, hollow valve body internally partitioned so as to form an inlet chamber and an outlet chamber. The inlet chamber is coupled to a ventricular catheter; the outlet chamber is coupled to a drainage catheter. The valve is designed for use in a hydrocephalus treatment system, for example, as shown in FIG. 1 of applicant's U.S. Pat. No. 3,527,226. The internal partitioning is accomplished by means of a thin, flat plate tightly fitting within the tubular valve body. This plate is provided with a circular aperture connecting the inlet and outlet chambers. A spherical ball of diameter larger than that of the aperture in the thin plate serves to restrict the flow through the aperture in a controlled manner. A spring, including a cantilevered flat portion overlying the ball and touching it at a single point biases it against the circular periphery of the flat plate aperture, effecting, when the valve is closed, a circular seal between the ball and aperture. This arrangement provides a precisely defined back pressure with low hysteresis and low susceptibility to clogging by debris. In a preferred embodiment the flat plate has a struck up rear portion which presses against the spring for adjusting the back pressure of the valve. In another embodiment, a screw threadably supported by the valve body, presses against the cantilevered portion of the spring permitting the back pressure of the valve to be accurately adjusted.

The effectiveness of the valve seal is tested during manufacture by optical means. Light energy at a wavelength for which the ball is opaque is directed upon the aperture with ball in place. Absence of light leakage indicates a properly sealing valve.

BRIEF DESCRIPTION OF THE DRAWING

The present invention will be better understood by reference to the following drawing in which:

FIG. 1 is a longitudinal sectional view of the valve device;

FIG. 2 is a sectional view of the valve device along section lines 2—2 of FIG. 1;

FIG. 3 is an edge view of the flat plate portion of the valve device;

FIG. 4 is a plan view of the flat plate portion of the valve device;

FIG. 5 is a schematic representation of the optical method for testing the sealing effectiveness of the valve device;

Corresponding reference characters indicate corresponding parts throughout the several views of the drawings.

DESCRIPTION OF THE PREFERRED EMBODIMENT

Figure 6:
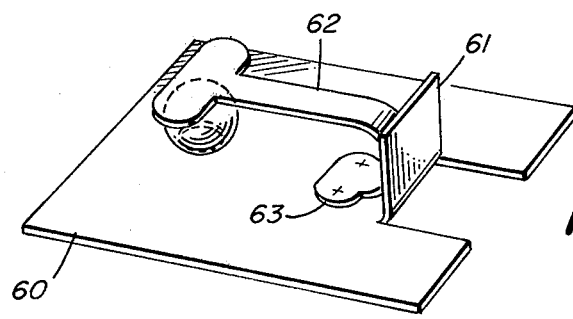
FIG. 6 is a perspective view of another embodiment of this invention.

Referring to FIGS. 1 and 2, a valve device 10 comprises a hollow valve body 11, preferably made of injection molded polyethersulfone plastic. Valve body 11 couples at its inlet end to a cerebroventricular catheter 12, and its outlet end with a drainage catheter 13 or with a pumping system, including a second valve, i.e., in the manner shown in U.S. Pat. No. 3,527,226. Tightly fitting within the valve body 11 is a thin, flat plate 14, preferably made of stainless steel, which partitions the valve body 11 into an inlet chamber 15 and an outlet chamber 16. In this embodiment, the thin plate 14 is 0.38 inch long, 0.14 inch wide and 0.01 inch thick. A highly polished circular aperture 17 of diameter 0.057 inch is cut through the flat plate 14 thereby connecting inlet chamber 15 and outlet chamber 16 providing a flow path for cerebrospinal fluid from the cerebral ventricles to drainage into the circulatory system. As can be seen more clearly in FIG. 3, circular aperture 17 in flat plate 14 has a coined rim 18, the radius of curvature of which matches the radius of a spherical ball 19, thereby providing a seat for the ball 19. In this embodiment, the radius of curvature of rim 18 is approximately 0.620 inch. The combination of valve body 11 and thin plate 14 allows this shunt valve to be light in weight, compact and inexpensive to manufacture.

Spherical ball 19 for controllably restricting flow through the valve is a highly polished hard material, preferably ruby or synthetic sapphire, having a diameter of 0.620 inch which is larger than the diameter of aperture 17 so that it rests against coined rim 18 of aperture 17 without passing through, thereby forming a seal. The highly polished surfaces of ball 19 and aperture 17 ensure an effective seal when ball 19 is seated, and furthermore, lessen any tendency for the ball to become stuck in the seated position, so enabling a precisely defined and repeatable opening pressure.

Referring now to FIG. 1 and FIG. 4, a flat spring 20, having a semicircular bend, is attached to flat plate 14 at 21 by spot welding or other suitable means. The constant of the spring 20 may be varied by altering its width or thickness, thereby allowing for valves with different operating pressures. Spring 20, parallel to the plane of aperture 17, overlies ball 19, touching it at essentially a single point and biasing it against rim 18 of aperture 17. This arrangement achieves a narrow hysteresis between opening and closing pressures. When the valve is open, ball 19 is able to spin freely because of the point contact with spring 20, discouraging the accumulation of debris and permitting close regulation of the back pressure presented to the lateral ventricles.

Valve 10 is assembled by inserting the flat plate-ball-spring assembly into valve body 11 from the right side of FIG. 1. The contour of chamber 16 is such that ball 19 will remain within aperture 17 after assembly. That is, shoulder 28 limits the extension of spring 20, thereby assuring that ball 19 cannot become dislodged from aperture 17.

In FIG. 5, the method of testing the sealing characteristics of the shunt valve disclosed herein is illustrated. Light source 25 illuminates one side of flat plate 14 with the ball 19 seated. The wavelength of the light from source 25 is selected so that ball 18 is opaque. With a sapphire ball, for example, green light is appropriate. A light detector 26 is arranged on the opposite side of flat plate 14 to detect any light which passes through aperture 17 of flat plate 14. Absence of light reaching the detector indicates a properly sealing valve.

In addition to adjusting back pressure by selecting the width or thickness of the ball-biasing spring, fine adjustments can be achieved with the embodiment of the invention shown in FIG. 6. In FIG. 6, a flat plate 60 has a struck up rear portion 61 which presses against the semicircular bend in a spring 62. To establish a desired value of back pressure, the spring 62 is first attached to flat plate 60 at 63 by spot welding or other suitable means. The struck up portion 61 is then forced (by means of a conventional tool not shown) beyond its elastic limit so as to take a set against the spring 62. The spring constant of the spring 62 is thereby altered depending on the degree to which the struck up portion 61 is deformed to press against the semicircular bend in the spring 62. Thus, by adjusting the level of force with which the struck up portion 61 engages the spring 62, the operating back pressure of a valve incorporating the elements depicted in FIG. 6 may be very precisely set. An alternative way of accurately establishing a desired back pressure will now be described, still with reference to FIG. 6. Instead of first attaching the spring 62 to the flat plate 60, the struck up portion 61 is put into place, for example, oriented perpendicularly to the flat plate 60. The semicircular bend of spring 62 is then forced against the struck up portion 61 while the spring's operating pressure is continuously measured by conventional means. When the desired operating back pressure is attained, the spring 62 is then secured to the flat plate 60, as by spot welding at 63. The use of a struck up portion of the flat plate to adjust operating pressure is superior to attempting to alter operating pressure by deforming the spring 62 itself. This is the case because the thin spring material, having a large elastic limit, is difficult to deform with precision so as to achieve a desired operating pressure.

Figure 7:
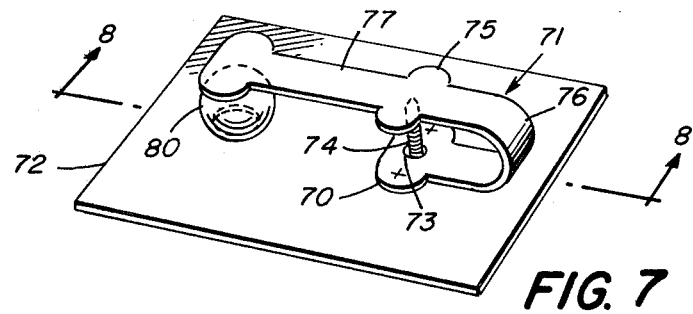
FIG. 7 is a perspective view of yet another embodiment.
Figure 8:
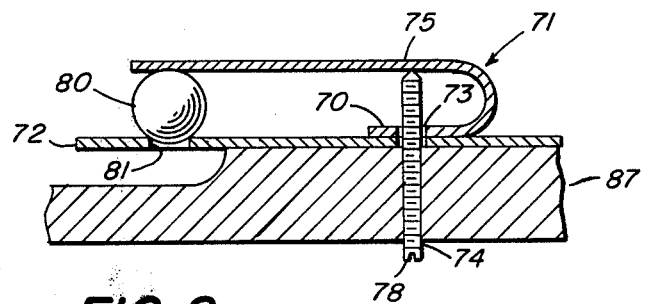
FIG. 8 is a sectional view along section lines 8—8 of FIG. 7.

Yet another embodiment of the invention allowing for accurate setting of the operating back pressure is shown in FIGS. 7 and 8. A base portion 70 of a spring 71 is attached, as by spot welding, to a flat plate 72. The base portion 70 has a hole 73 through which passes a screw 74. The screw 74 rests against an enlarged section 75 of the spring 71. The spring 71 also includes a wider, relatively stiff part 76 and a narrower section 77 which overlies a ball 80. As can be seen in FIG. 8, the screw 74 is threadably supported in a valve body 77 so that by inserting a tool (not shown) into a slot 78, the screw 74 may be rotated to adjust the degree to which it presses on the enlarged section 75 of the spring 71. In this way, the "popping" pressure of the ball 80 in an aperture 81 may be very accurately adjusted. In this embodiment, the operating pressure can be varied as desired during the operating lifetime of the valve.

Although in these embodiments, injection molded polyethersulfone plastic has been used for valve body 11 and stainless steel for flat plate 14 and spring 19, it is obvious that other stable, essentially inert and non-toxic materials could be utilized. Similarly, although ruby is the preferred material for ball 19, other hard, non-toxic and inert materials such as synthetic sapphire could be substituted.

The disclosed valve is, therefore, compact, light in weight, inexpensive to manufacture and simple to assemble. More importantly, the valve achieves a tight regulation of the cerebrospinal fluid pressure within the cerebral venticles.

While the above describes and illustrates a preferred embodiment of the invention, it is to be understood that the invention is not so limited, but covers all modifications which should be apparent to one skilled in the art and falling within the scope of the invention.

We claim:

1. In a surgically implantable shunt system in which cerebrospinal fluid is vented from a cerebroventricular catheter to a drainage catheter, a valve for presenting a precisely controllable back pressure to the ventricles, said valve comprising:

an elongate, hollow valve body;

a flat plate partitioning said valve body so as to form an inlet chamber and an outlet chamber, said ventricular catheter being coupled so said inlet chamber and said drainage catheter being coupled to said outlet chamber, said plate being provided with a circular aperture connecting said inlet and outlet chambers;

a spherical ball of diameter larger than said aperture for controllably restricting flow through said aperture; and a spring including a cantilevered flat portion overlying said ball and biasing it against the circular periphery of said aperture whereby a circular seal is selectively effected between said ball and said plate, providing a precisely defined back pressure with low hysteresis and low susceptibility to bridging by debris.

2. In a surgically implantable shunt system in which cerebrospinal fluid is vented from a cerebroventricular catheter to a drainage catheter, a valve for presenting a precisely controllable back pressure to the ventricles, said valve comprising:

an elongate, hollow valve body;

a stainless steel flat plate partitioning said valve body so as to form an inlet chamber and an outlet chamber, said ventricular catheter being coupled to said inlet chamber and said drainage catheter being coupled to said outlet chamber, said plate being provided with a highly polished circular aperture connecting said inlet and outlet chambers;

a highly polished, spherical sapphire ball of diameter larger than said aperture for controllably restricting flow through said aperture; and a metallic spring including a cantilevered flat portion parallel to the plane of said aperture overlying said ball and biasing it against the circular periphery of said aperture whereby a circular seal is selectively effected between said ball and said plate, providing a precisely defined back pressure with low hysteresis and low susceptibility to bridging by debris.

3. The valve of claim 2 wherein said flat plate is approximately 0.01 inch thick.

4. The valve of claim 2 wherein said circular aperture is approximately 0.057 inch in diameter and said ball is approximately 0.620 inch in diameter.

5. The valve of claim 1 wherein said flat plate includes a struck up rear portion said struck up portion adapted to apply an adjustable level of force against said spring to establish a desired value of said back pressure.

6. The valve of claim 1 wherein said flat plate includes a struck up rear portion, and said spring includes a semicircular bend and is adapted for attachment to said flat plate; wherein said spring is attached to said flat plate at a location so that said semicircular bend presses against said struck up rear portion so as to establish a desired value of said back pressure.

7. The valve of claim 1 further including screw means threadably supported by said valve body and adapted for adjustably pressing against said cantilevered flat portion of said spring to establish a desired value of said back pressure.

* * * * *